United States Patent [19]

Jeram et al.

[11] 3,957,713

[45] *May 18, 1976

[54] HIGH STRENGTH ORGANOPOLYSILOXANE COMPOSITIONS

[75] Inventors: Edward M. Jeram, Burnt Hills; Richard A. Striker, Troy, both of N.Y.

[73] Assignee: General Electric Company, Waterford, N.Y.

[ * ] Notice: The portion of the term of this patent subsequent to May 20, 1992, has been disclaimed.

[22] Filed: Aug. 12, 1974

[21] Appl. No.: 496,752

Related U.S. Application Data

[63] Continuation of Ser. No. 351,107, April 13, 1973, Pat. No. 3,884,866.

[52] U.S. Cl. .................. 260/32.8 SB; 260/33.6 SB; 260/37 SB
[51] Int. Cl.² .......................................... C08K 5/07
[58] Field of Search .......... 260/33.6 SB, 37 SB, 825, 260/32.8 SB

[56] References Cited
UNITED STATES PATENTS

| | | | |
|---|---|---|---|
| 3,220,972 | 11/1965 | Lamoreaux | 260/33.6 SB X |
| 3,436,366 | 4/1969 | Modic | 260/825 X |
| 3,699,073 | 10/1972 | Wada et al. | 260/825 X |
| 3,884,866 | 5/1975 | Jeram et al. | 260/32.8 SB |

*Primary Examiner*—Lewis T. Jacobs
*Attorney, Agent, or Firm*—Donald J. Voss; E. Philip Koltos; Frank L. Neuhauser

[57] ABSTRACT

There is provided an organopolysiloxane composition combining high strength with exceptionally good elongation, which composition comprises a first component, a mixture of two vinyl-containing polysiloxanes or blends of vinyl-containing polysiloxanes, one of which is a high viscosity polysiloxane or a blend of high viscosity polysiloxanes, the other is a low viscosity polysiloxane or a blend of low viscosity vinyl-containing polysiloxanes, a filler and an effective amount of a platinum catalyst.

The second component comprises a hydrogen-containing silane or polysiloxane. When it is desired to cure the composition into an elastomer the first component is mixed with the second component, that is, the hydrogen containing silane or polysiloxane and the mixture is allowed to cure either at room temperature or at elevated temperatures. Part of the total high viscosity vinyl-containing polymer can be mixed with the second component.

9 Claims, No Drawings

HIGH STRENGTH ORGANOPOLYSILOXANE COMPOSITIONS

This application is a continuation of application Ser. No. 351,107, filed Apr. 13, 1973, now U.S. Pat. No. 3,884,866, issued May 20, 1975.

BACKGROUND OF THE INVENTION

The present invention relates to an organopolysiloxane elastomer which is prepared through an SiH olefin addition reaction and more particularly the present invention relates to an organopolysiloxane elastomer which is prepared through an SiH olefin addition in the presence of a platinum catalyst to result in an elastomer with high tensile strength, good elongation and high tear.

At the present time, there has been produced various silicone gels which are used for orthopedic devices or prosthetic devices. It has been found highly desirable to encase such orthopedic gels in a film of material so that the resulting gel could be used as an orthopedic device or prosthetic device. It was desired that the film of material have a high tensile strength, a good elongation and a high tear so that the film even in small thicknesses could not be punctured accidentally and the gel allowed to leak out requiring frequent repairs of the orthopedic or prosthetic device.

One attempt to provide such a film was the use of heat vulcanizable silicone rubber compositions. Although such films could possibly be prepared through the use of heat vulcanizable silicone rubber compositions it was found that such heat vulcanizable silicone rubber compositions were difficult to work with and especially in preparing films of small thicknesses such as 6 to 25 mils. In addition, heat cured rubber has low elongations.

Other organopolysiloxane compositions such as room temperature vulcanizable silicone rubber compositions were tried to prepare such films with the same difficulties as was experienced with heat vulcanizable silicone rubber compositions.

In addition, traditional SiH-olefin addition reaction products were tried to produce the required films or coatings. However, such traditional SiH olefin addition elastomeric compositions were found not to have as high a tensile as would be desired and more specifically were found to have a low elongation and a low tear.

Accordingly, it was highly desirable to discover a silicone rubber composition which would cure quickly, if desired, at elevated temperatures and would require no post baking as is traditional with heat vulcanizable silicone rubber compositions.

It was also desirable to prepare a silicone rubber composition which could be injection molded. Most silicone rubber compositions and particularly heat vulcanizable silicone rubber compositions because of their high viscosity are very difficult to injection mold and require excessively high pressure such as, 40,000 psi and even higher. In addition, such heat vulcanizable silicone rubber compositions are difficult to injection mold so as to form intricate parts, and they require special molds that are to be used in the injection molding as well as long times to cure at elevated temperatures.

Accordingly, it is one object of the present invention to provide for an SiH olefin addition elastomeric silicone rubber composition which in the cured state has a combination of high tensile strength, high elongation and high tear compared to that of the best heat vulcanizable silicone rubber compositions.

In addition, it is another object of the present invention to provide for an SiH olefin addition silicone rubber composition that can be used to form films or coatings of exceptionally high strength, high elongation and high tear, which coatings and films are easy to form and can be cured either at room temperature or at an exceedingly fast rate at elevated temperatures.

It is still an additional object of the present invention to provide for an SiH olefin addition silicone rubber composition which is especially suited for low pressure injection molding to form any type of parts and which composition can be cured at a very fast rate at elevated temperatures.

These and other objects of the present invention are accomplished by means of the composition set forth hereinbelow.

SUMMARY OF THE INVENTION

There is provided by the present invention an organopolysiloxane composition combining high strength with exceptionally good elongation and tear comprising (A) 100 parts of a first component having therein (i) 20 to 90 parts of a vinyl-containing high viscosity organopolysiloxane or a blend of high viscosity vinyl-containing polysiloxanes having no more than 25 mole percent or phenyl radicals and having a viscosity of 5,000 to 1,000,000 centipoise at 25°C of the formula,

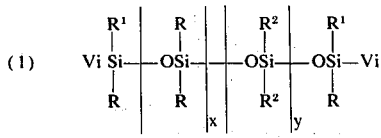

where Vi stands for vinyl, $R^1$ is selected from the class consisting of lower alkenyl, alkyl and aryl radicals and R is selected from the class consisting of monovalent hydrocarbon radicals and halogenated monovalent hydrocarbon radicals, $R^2$ is selected from the class consisting of alkyl and aryl radicals, $x$ varies from 100 to 10,000 and $y$ varies from 0 to 300. This high viscosity vinyl-containing organopolysiloxane is mixed with (ii) from 5 to 40 parts of a low viscosity vinyl-containing organopolysiloxane or a blend of low viscosity polysiloxanes having a vinyl content that may vary from 0.01 mole percent vinyl to 60 mole percent vinyl and a viscosity that varies from 50 to 5,000 centipoise at 25°C and having no more than 25 mole percent phenyl radicals of the formula,

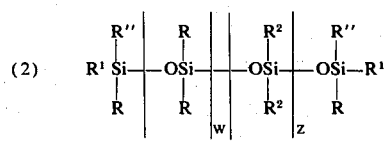

wherein $R^1$, $R^2$ and R are as previously defined, $R''$ is selected from the class consisting of alkyl, aryl and alkenyl radicals, $w$ varies from 0 to 500 and $z$ varies from 0 to 200; and these two vinyl-containing organopolysiloxanes are mixed with (iii) from 5 to 70 parts of a filler; (iv) from 0.1 to 50 parts per million of the total organopolysiloxane composition of a platinum catalyst which may be any type of known platinum catalyst such as, chloroplatinic acid. Per 100 parts of (A) composition and at the time there is desired to cure the composition there may be mixed the second component of this composition which comprises from 1 to 100 parts based on 100 parts of (A) of a second component (B) which is a hydrogen silicone composition selected from the class consisting of hydrogen containing silanes and hydrogen containing polysiloxanes and mixtures of hydrogen containing polysiloxanes with fillers and high viscosity polysiloxanes. Hydrogen containing polysiloxanes are the preferred second component (B). This composition when the two components are mixed together may either be cured at room temperature for 17 hours to produce the desired composition or may be cured at elevated temperatures such as, 300°C for 10 seconds. Note — when only a hydrogen polysiloxane is present in component (B) that B is preferably present at a concentration of 1 to 10 parts per 100 parts of component (A) but that when a part of the filler and/or high viscosity vinyl-containing polysiloxane is mixed in with component (B) there may be used 100 parts of component (B) per 100 parts of component (A).

The filler that is used in this composition and particularly in component (A) is preferably a silica filler that has been treated such as, silazane treated silica filler. Component (A) and component (B) may be dissolved in a solvent such as, hexane, octane and etc. to form two solutions and then when the composition is ready to be used to form a coating or a film, the two solutions are thoroughly mixed together and then a part in the shape it is desired to form the film is dipped into the solution one or more times to deposit a sufficiently thick film which can then be allowed to air dry so that the solvent evaporates and the organopolysiloxane mixture is allowed to cure to an elastomeric film.

In another embodiment the mixture of the two solutions may be applied over any surface in the thickness desired and then the solvent can be allowed to evaporate so as to leave the desired coating on the object to which the solution was applied which coating will cure to an exceptionally high strength, high elongation and high tear silicone elastomeric composition.

DESCRIPTION OF THE PREFERRED EMBODIMENT

The radical R in Formulas (1) and (2) is selected from monovalent hydrocarbon radicals and halogenated monovalent hydrocarbon radicals, that is, radicals normally associated as substituent groups for silicone polysiloxanes. Thus, the radical R in the vinyl containing polysiloxanes of Formulas (1) and (2) may be individually selected from the class consisting of mononuclear and bi-nuclear aryl radicals such as, phenyl, tolyl, xylyl, naphthyl and etc.; halogenated mononuclear and binuclear aryl radicals such as, chlorophenyl, chloronaphthyl, and etc.; mononuclear aryl lower alkyl radicals having from 1 to 8 carbon atoms per alkyl groups such as, benzyl, phenyl and etc.; lower alkyl radicals having from 1 to 8 carbon atoms such as, methyl, ethyl, propyl, butyl, pentyl, hexyl, octyl and etc.; lower alkenyl radicals having from 2 to 8 carbon atoms such as, vinyl, allyl and 1-propenyl; halo lower alkyl radicals having from 1 to 8 carbon atoms such as, chloropropyl, trifluoropropyl and cycloalkyl radicals such as, cyclobutyl, cyclopentyl and cyclohexyl. Preferably, the R radical in the vinyl containing polysiloxanes of Formulas (1) and (2) is a lower alkyl radical of 1 to 8 carbon atoms such as, methyl, ethyl and phenyl.

The radical $R'$ in Formulas (1) and (2) is selected from the class consisting of lower alkenyl of 2 to 8 carbon atoms, lower alkyl of 1 to 8 carbon atoms and mononuclear aryl radicals. Preferably, the radical $R'$ in Formulas (1) and (2) is a lower alkenyl radical such as, vinyl, allyl and etc.

The radical $R^2$ in the vinyl containing polysiloxanes of Formulas (1) and (2) is preferably an alkyl radical or a mononuclear aryl radical and is more preferably a lower alkyl radical of 1 to 8 carbon atoms or a phenyl radical. It should be, of course, realized that there are two $R^2$ radicals in each silicone atom, the two $R^2$ radicals can be the same or different. Preferably, the $R^2$ radical is a phenyl radical taking into consideration that each vinyl-containing polysiloxane of Formulas (1) and (2) may not have more than 25 mole percent of phenyl radicals.

The $R''$ radical in Formula (2) is selected from the same groups as the $R^1$ radical, that is, groups selected from the class consisting of alkyl, aryl and alkenyl radicals and the $R''$ radical is preferably selected from the class consisting of lower alkyl radicals of 1 to 8 carbon atoms, phenyl radicals and lower alkenyl radicals of 2 to 8 carbon atoms. Most preferably, the $R''$ radical is selected from methyl, ethyl, propyl, vinyl and allyl.

The essence of the present invention and particularly the way the present invention distinguishes from the SiH olefin addition silicone rubber compositions of the prior art is the presence in the composition of the present case of two vinyl containing polysiloxanes, one of which is a high viscosity vinyl containing polysiloxane or a blend of high viscosity vinyl containing polysiloxanes of Formula (1) and the other one which is a low viscosity vinyl containing polysiloxane or a blend of low viscosity vinyl containing polysiloxanes of Formula (2). The high viscosity vinyl containing polysiloxane generally may have a viscosity of 5000 to 1,000,000 centipoise at 25°C and more preferably has a viscosity from 10,000 to 500,000 centipoise at 25°C. In such a vinyl containing polysiloxane, that is, the vinyl containing polysiloxane of Formula (1), as has been stated, $x$ varies from 100 to 10,000 and $y$ varies from 0 to 300. More preferably, $x$ varies from 500 to 2000 and $y$ varies from 0 to 100. This high viscosity vinyl containing polysiloxane or blend of vinyl containing polysiloxanes which has at least one vinyl group at the terminal position of the polysiloxane chain is blended and mixed with a low viscosity polysiloxane or blend of low viscosity polysiloxanes which may have one vinyl group at the terminal position of the polysiloxane chain and may have two vinyl groups at the terminal position of the polysiloxane chain.

The low viscosity vinyl containing polysiloxane of Formula (2) may contain anywhere from 0.01 mole percent vinyl to 60 percent vinyl and more preferably contains from 2 to 15 mole percent vinyl. This low viscosity vinyl containing polysiloxane may have a viscosity that varies from 50 to 5,000 centipoise and more preferably varies from 50 to 1,000 centipoise at 25°C. In Formula (2), $w$ generally varies from 0 to 500 and $z$ varies from 0 to 200. More preferably, $w$ varies from 50 to 300 and $z$ varies from 0 to 100.

In the mixture of these vinyl containing polysiloxanes, that is, 100 parts of component (A), there is preferably from 5 to 40 parts and more specifically 10 to 25 parts of the low viscosity vinyl containing polysiloxane in composition with generally from 20 to 90 parts of the high viscosity vinyl containing polysiloxane and more preferably from 30 to 80 parts of the high viscosity vinyl containing polysiloxane. Such a mixture results in the resulting cured composition having exceptionally good tensile strength, elongation and tear strength properties. Thus, the cured composition will have a tensile strength of approximately 1,000 psi or more, an elongation of 1,000 percent or more, and a tear of 200 lbs/in pi or more. It has been found that with this combination of vinyl containing polysiloxanes it is possible to obtain a cured elastomeric product that has these high values for tensile strength, elongation and tear and still have a low hardness, that is, the hardness of the cured composition may be varied from a value as low as 10 up to 65 or more. The advantage of obtaining a low hardness for the composition of the instant case is that it can be used to form coatings which enclose gels so as to form various prosthetic devices and orthopedic devices which will feel soft and not hard to the human skin.

In component (B) there must be present an SiH material, that is, a silicone material containing hydrogen groups. Thus, in the SiH material there is preferably one hydrogen atom for every vinyl group in both the low viscosity vinyl containing polysiloxane of Formula (2) and also for every vinyl group in the high viscosity vinyl containing polysiloxane of Formula (1). Although the hydrogen containing silicone material may be a silane it is most advantageous, either a hydrogen containing polysiloxane resin or a hydrogen containing polysiloxane linear polymer.

Thus, in one of the embodiments of the present invention, the SiH material of component (B) may be a polysiloxane resin having the formula $H(R^3)_2SiO_{1/2}$ units and $SiO_2$ units where the ratio of the monofunctional units to tetrafunctional units may vary from 0.5:1 to 10:1, and is preferably about 2:1. The hydroxyl and alkoxy content of such a resin is preferably less than 0.5 weight percent based on the weight of the resin. The $R^3$ radical is selected from the class consisting of hydrogen, monovalent hydrocarbon radicals and halogenated monovalent hydrocarbon radicals. Thus, the radical $R^3$ may be selected from the same radicals as discussed above with respect to the R radical appearing in Formulas (1) and (2) and may in addition be hydrogen. Preferably, the $R^3$ radical is a lower alkyl radical of 1 to 8 carbon atoms such as, methyl, ethyl and etc.

In addition to the hydrogen containing silicone resin defined above which is comprised of monofunctional units and tetrafunctional units, there may be utilized a hydrogen containing linear polysiloxane such as that of the formula,

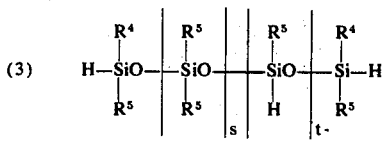

(3)

wherein $R^4$ is selected from the class consisting of hydrogen, monovalent hydrocarbon radicals and halogenated monovalent hydrocarbon radicals, that is, the same radicals, with the exception of hydrogen, as the R radicals which were defined above with respect to the vinyl containing polysiloxanes of Formulas (1) and (2). The $R^5$ radical is selected from the class consisting of monovalent hydrocarbon radicals and halogenated monovalent hydrocarbon radicals, that is, the same radicals that were defined with respect to the R radical, in connection with the definition of the compounds of Formulas (1) and (2), s varies from 1 to 1000 and t varies from 5 to 200. More preferably, s varies from 10 to 500 and t varies from 5 to 200.

With respect to the hydrogen containing polysiloxane of Formula (3), note that such a polysiloxane which forms component (B) in the present composition must have at least two hydrogen atoms attached to the terminal silicone atoms in the polysiloxane chain. Preferably, such a hydrogen containing polysiloxane of Formula (3) has at least two hydrogen atoms connected to the silicone atoms in the external portion of the polysiloxane chain.

The preparation of the polysiloxanes of Formulas (1), (2) and (3) is well known in the art. Such polysiloxanes are formed by taking the appropriate halosilanes and first hydrolyzing them in water, then adding to the hydrolyzate a catalyst such as KOH and heating the resulting mixture at elevated temperatures so as to form a large amount of the desired cyclic polysiloxanes which are stripped off and collected. The resulting cyclic polysiloxanes are then taken and placed in a reaction chamber in the presence of a small amount of siloxane rearrangement catalyst such as, acid catalyst in the case of the hydrogen polysiloxanes of Formula (3) and KOH in the case of the polysiloxanes that is desired to be produced of Formulas (1) and (2), which may be present at a concentration of anywhere from 10 to 100 parts per million. To the cyclic polysiloxanes and catalyst there is added the desired type and amount of end-stoppers so as to form the polysiloxanes coming within the scope of Formulas (1), (2) and (3), with the desired viscosity. Thus, hydrogen containing disiloxanes and vinyl containing disiloxanes are added to the chosen cyclic polysiloxanes; the vinyl containing disiloxanes being added in the case where it is desired to produce a polysiloxane Formulas (the scope of Formulas(1) and (2) and the hydrogen disiloxanes being added when it is desired to produce the hydrogen containing polysiloxanes of Formula (3). The resulting end-stoppers and cyclic polysiloxanes are then cooked at elevated temperatures such as, temperatures of above 150°C, until 85 percent of the cyclics have been formed into desired linear polysiloxanes of Formulas (1), (2) and (3) as the case may be. At this 85 percent equilibration point there are just as many linear polysiloxanes being formed from the cyclic polysiloxanes as there is cyclic polysiloxanes being formed from the linear siloxanes. At this point, there is then added sufficient amount of a neutralization agent such as, phosphoric acid or $NaHCO_3$ as the case may be, to the equilibration mixture so as to neutralize the catalyst. Then the remaining cyclics are stripped off and removed from the mixture. What is then left is the desired compound coming within the scope of Formulas (1), (2) and (3), as the case may be, which compounds may then be utilized in the compositions of the instant case.

The hydrogen containing siloxane resin containing monofunctional units and tetrafunctional units may be produced by methods well known in the art such as that, for instance, disclosed in Goodwin, U.S. Pat. No. 2,857,356. Such resins are formed by taking the appropriate halosilanes such as, for instance, hydrogendimethylchlorosilane and sodium silicate or ethyl orthosilicate and taking these reactants and adding them in the appropriate steps to a solution of hydrochloric acid in water, the orthosilicate being added first and then the hydrogendimethylchlorosilane being added in the second step. This hydrolysis mixture may optionally include a hydrocarbon solvent such as toluene, xylene and etc. The resulting hydrolyzates that are formed in the heterogenous hydrolysis mixture is then collected in the organic solvent phase and concentrated to the desired amount of solids. It is necessary before such a resin is used that most of the hydroxyl and alkoxy groups be removed from the resin. It is, of course, obvious that the amount of monofunctional constituent that is added to the tetrafunctional constituent will control the final ratio of monofunctional units to tetrafunctional units in the silicone resin product.

Accordingly, the hydrolyzate which as been removed in the organic solvent is then taken and there is added to it a bodying catalyst such as, 5 parts to 10 parts per million of acid and the resulting resin is heated at elevated temperatures such as, above 150°C, for a period of time of 1 to 10 hours until there is left less than 0.5 weight percent of alkoxy and hydroxyl groups in the resin product. The resin product may then be concentrated to the desired solid content such as, 100 percent solids content, and then be utilized in a 100 percent solids state to form the composition of the instant case.

It should be noted that component (A) and component (B), which is either the hydrogen polysiloxane resin or the hydrogen containing linear polysiloxane is utilized at a concentration of anywhere from 1 to 100 parts per 100 parts of component (A) and is more preferably utilized at a concentration of 1 to 50 parts per 100 parts of component (A). It is noted that component (A) and component (B) of the present composition can be mixed together and allowed to cure for 16 hours at room temperature. If it is desired to have the composition cure at a faster rate, it can be heated at elevated temperatures whereupon it will cure at a faster rate. For instance, at a temperature of 300°C, the composition prepared by mixing components (A) and (B) will cure to a hard desired elastomeric product in 10 seconds, thus making it highly suitable for injection molding.

In the composition of the present case there is mixed with component (A), a platinum catalyst for curing the component (A) with component (B) to an elastomeric state. Any type of platinum catalyst may be used at a concentration of anywhere from 0.1 to 50 parts per million of platinum based on the total weight of component (A) and component (B). Preferably, there is utilized at a concentration of anywhere from 0.1 to 10 parts per million of platinum based on the total weight of components (A) and (B).

Many types of platinum compounds for this SiH olefin addition reaction are known and such platinum catalysts may be used also for the reaction of the present case. The preferred platinum catalysts especially when optical clarity is required are those platinum compound catalysts which are soluble in the present reaction mixture. The platinum compound can be selected from those having the formula $(PtCl_2.Olefin)_2$ and $H(PtCl_3.Olefin)$ as described in U.S. Pat. No. 3,159,601, Ashby. The olefin shown in the previous two formulas can be almost any type of olefin but is preferably an alkenylene having from 2 to 8 carbon atoms, a cycloalkenylene having from 5 to 7 carbon atoms or styrene. Specific olefins utilizable in the above formulas are ethylene, propylene, the various isomers of butylene, octylene, cyclopentene, cyclohexene, cycloheptene, etc.

A further platinum containing material usable in the composition of the present invention is the platinum chloride cyclopropane complex $(PtCl_2.C_3H_6)_2$ described in U.S. Pat. No. 3,159,662, Ashby.

Still, further, the patent containing material can be a complex formed from chloroplatinic acid with up to 2 moles per gram of platinum of a member selected from the class consisting of alcohols, ethers, aldehydes and mixtures of the above as described in U.S. Pat. No. 3,220,972, Lamoreaux.

All the patents and patent applications mentioned in this present specification are incorporated into the present application by reference. tetravinylcyclotetrasiloxane The preferred platinum compound to be used not only as a platinum catalyst but also as a flame retardant additive is that disclosed in French Pat. No. 1,548,775, Karstedt. Generally speaking, this type of platinum complex is formed by reacting chloroplatinic acid containing 4 moles of water of hydration with tetravinylcycloetrasiloxane in the presence of sodium bicarbonate in an ethanol solution.

In order to get the high desired tensile strength in the compositions of the instant case and particularly when such compositions are formed to thin coatings or films, it is desirable to incorporate a filler into the composition. Illustrative of the many fillers which can be employed are titanium dioxide, lithopone, zinc oxide, zirconium silicate, silica aerogel, iron oxide, diatomaceous earth, calcium carbonate, fumed silica, silazane treated silica, precipitated silica, glass fibers, magnesium oxide, chromic oxide, zirconium oxide, aluminum oxide, alpha quartz, calcined clay, asbestos, carbon, graphite cork, cotton, synthetic fibers and etc.

The preferred fillers that should be utilized in the composition of the instant case and particularly in component (A) of the instant case, is preferably either a fumed silica or a precipitated silica that has been treated. Thus, the silica fillers may be treated as, for example, as disclosed in U.S. Pat. No. 2,938,009, Lucas with cyclic polysiloxanes Another method for treating fillers or treated fillers that can be utilized in the invention of the instant case is that disclosed in Brown U.S. Pat. No. 3,024,126, disclosure of which patents are incorporated into the present case by reference.

More specifically, silazane treated fillers in accordance with the disclosure of Smith, U.S. Pat. No. 3,635,743 and Beers, patent application, Ser. No. 311,486, filed Dec. 4, 1972, are preferred as the treated fillers to be utilized in the compositions of the present case.

These fillers are generally utilized in a concentration of 5 to 70 parts of treated filler for each 100 parts of component (A). More preferably, the filler is utilized at a concentration of 10 to 40 parts of filler present per 100 parts of component (A). One of the advantages of the silicone composition of the instant case is that it will form a high strength, high elongation, high tear elastomeric film even at low concentrations of silica filler. In some cases, high concentrations of silica filler are not desired in the silicone rubber compositions of the instant case since they will tend to increase the hardness of the cured elastomer. Many well known ingredients can be added to the composition of the instant case. For instance, the usual additives and other ingredients which are added to prior art SiH olefin addition elastomeric silicone rubber compositions can also be added to the composition of the instant case without any deleterious effects, such ingredients such as, pigments, heat stabilizing agents, such as, iron oxide and etc.

The ingredients present in component (A) and component (B), that is, component (B) comprises the hydropolysiloxane or a mixture of the hydropolysiloxane, filler and/or vinyl containing polysiloxane and component (A) comprising the high viscosity vinyl containing polysiloxane, the low viscosity vinyl containing polysiloxane, filler and platinum catalyst, are kept separate until it is desired to prepare a cured elastomeric polysiloxane composition. Thus, the ingredients of component (A), the platinum catalyst, filler and vinyl containing polysiloxanes, are intimately mixed with each other as well as with any other additional ingredients to form component (A), which is then stored until it is desired to prepare the cured composition. Component (B) is also prepared and stored separate from component (A) until it is desired to form the cured silicone rubber composition. When it is desired to form the cured silicone rubber composition, the two components are mixed into each other and the composition is allowed to cure either for 16 hours at room temperature or at elevated temperatures for the desired period of time to form the cured elastomer.

One advantageous way of forming an elastomeric film or coating of the compositions of the instant case is to dissolve component (A) and component (B) in a diluent or organic solvent. The two components may be dissolved in the solvent at any time and kept separate prior to cure for long periods of time without any deleterious effects, that is, without the solution gelling or the composition curing. Then the two solutions at the desired point of time when it is desired to form the film or coating may be mixed together to form one solution and the resulting solution applied to a surface at the desired rate. Then the solvent may be allowed to evaporate and allow components (A) and (B) which were in the solution and which are thoroughly mixed together to cure to form an elastomeric film or coating.

Another method that may be used is to dip an article into the resulting solution of components (A) and (B), that is, a formed object in the shape in which it is desired to form a film, may be dipped into the solution as many times as is necessary until the proper thickness of film has been formed on the formed object. The object may then be heated at elevated temperatures or allowed to stand at room temperature until the solvent evaporates off and the composition of the instant case cures to form an elastomeric film of very high tensile strength, high elongation, high tear and which is also desirably of low hardness. Solvents which may be utilized to dissolve in components (A) and (B) of the present composition are any of the common organic solvents for the prior art SiH olefin addition reactants. Such solvents are, for example, hexane, heptene, pentane, octane, cyclohexane, toluene, xylene, benzene, acetone, as well as other well known nonhalogenated hydrocarbon solvents.

The following examples are presented for the purpose of illustrating the present invention and are not meant in ay way or manner to limit the scope of the present specification or claims.

EXAMPLE 1

There was formed a component (A) in which in 100 parts of such component (A) there was present 20.6 parts by weight of a high viscosity vinyl containing polysiloxane of the formula,

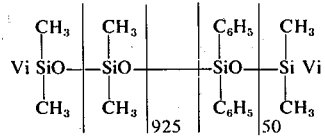

This vinyl containing polysiloxane had a viscosity of 60,000 centipoise at 25°C. To this vinyl containing polysiloxane there was added 5.1 parts of a low viscosity, that is, a 500 centipoise at 25°C viscosity, vinyl containing polysiloxane mixture of compounds of the formula,

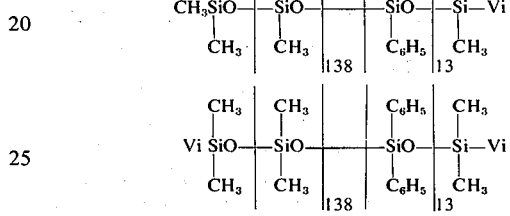

The low viscosity vinyl containing polysiloxane was a mixture of two compounds of the formulas as shown above. As stated, this low viscosity vinyl containing polysiloxane mixture has a viscosity of 500 centipoise at 25°C. It also contained 10 mole percent of phenyl, while the high viscosity vinyl containing polysiloxane contained 5.3 mole percent of phenyl radicals. To the mixture of these two vinyl containing polysiloxanes, there was added 7.7 parts of silazane treated silica filler, the silazane treated being treated as disclosed in Smith, U.S. Pat. No. 3,635,743. To this mixture there was then added 7 parts per million of platinum in the form of a platinum complex such as that disclosed in U.S. Pat. No. 3,220,972, Lamoreaux. These ingredients were mixed together and then dissolved in 66.6 parts of hexane. The resulting mixture comprised component (A).

Component (B) was then formed by taking a hydrosilane resin comprising $H(CH_3)_2SiO_{1/2}$ units and $SiO_2$ units where the ratio of the monofunctional units to the tetrafunctional units is 2:1, wherein the resin has substantially zero percent by weight hydroxyl groups. 0.8 parts of this resin was dissolved in 9.2 parts of hexane to form component (B). To 10 parts of the solution of component (B) there was mixed 100 parts of the solution of component (A) as prepared above. The resulting solution that was formed was then used to form 25 millimeter cured films. Such films were formed by repeated dippings of the formed part into the solution of components (A) and (B) until a film of about 25 mils thick was formed on the formed part. The resulting film of material on the formed part was then allowed to air dry for 24 hours at room temperature, that is, the formed part was allowed to stand at room temperature until all the solvent evaporated and until at the end of 24 hours there had been formed a cured elastomeric film on the formed part. This film was tested for its physical properties and the results are listed in Table I below.

Another 25 mil cured film was also formed from the same solution in the same way as the prior film, however, this film was cured at 16 hours at room temperature and then heated 1 hour at 95°C. The physical properties of this heat cured film is also listed in Table I below.

TABLE I

| Cure | 24 hrs. at R.T. | 16 hrs. at R.T. + 1 hr. at 95°C |
|---|---|---|
| Tensile, psi | 1000 | 1150 |
| Elongation, % | 1000 | 1000 |
| Durometer A | 23 | 26 |
| Tear, lbs./in. | 150 | 150 |
| Specific Gravity | 1.13 | 1.13 |

The results in Column I of Table I, above, indicate the outstanding properties that are inherent in films formed from the compositions of the present case and these properties hold true not only for films of 25 millimeter thickness and higher but also hold true for films that have a thickness as low as 6 millimeters. The results in Table I above, show that the elastomeric films produced by the compositions of the instant case have a very high tensile strength, high elongation, low hardness and a high tear and also have good heat aging properties. The properties may be compared with the prior art SiH olefin addition elastomers where typical properties of such SiH olefin addition elastomers are a Tensile Strength of 800 psi, an Elongation of 250 percent, a Shore A Hardness of 65, and a Tear of 100 lbs/in. Accordingly, with the compositions to the present invention it is possible to produce clear cured elastomeric films of thicknesses anywhere from 6 mils to up to 25 or more mils wherein such films have outstandingly high tensile strength, elongation and tear with a low value for hardness, that is, the films produced in accordance with the present invention are soft and not hard materials.

EXAMPLE 2

There was prepared 100 parts of a two component composition wherein component (A) comprised 61.8 parts of a high viscosity vinyl containing polysiloxane of the formula,

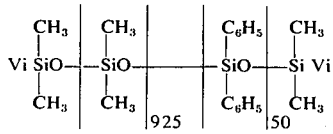

wherein such high viscosity vinyl containing polysiloxane had a viscosity of 60,000 centipoise at 25°C and contained 5.3 mole percent phenyl radicals. To this high viscosity vinyl containing polysiloxane there was mixed 15.2 parts of a blend of low viscosity vinyl containing polysiloxanes which blend had a resulting viscosity of 500 centipoise at 25°C and in which the vinyl containing polysiloxane comprised a mixture of compounds of the following formulas,

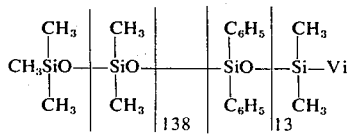

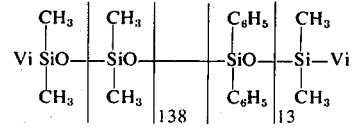

To these two components there was then added 23.0 parts of silazane treated silica filler treated in the same manner as that disclosed in Smith, U.S. Pat. No. 3,635,743. These ingredients were then dissolved in 200 parts of hexane. To this solution there was then added 6 parts per million based on the weight of the vinyl containing polysiloxanes in the form of a platinum complex such as that disclosed in Lamoreaux, U.S. Pat. No. 3,220,972, whose disclosure is hereby incorporated into the present example by reference. This solution then formed component (A) of a two component system of the present invention.

Component (B) was then formed by dissolving .8 parts of a hydrogen linear polysiloxane of the formula,

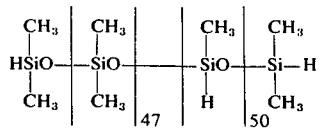

In 9.8 parts of hexane to form a solution that comprised component (B) of the present invention. To 10 parts of this solution there was mixed 100 parts of the solution of component (A). The resulting solution was then taken and there was dipped into it a formed part with repeated dippings into the solution until there was formed on the formed part a film of about 6 mils thick. The resulting film was allowed to cure at room temperature for 24 hours and as it cured at room temperature the solvent evaporated and allowed the composition of the present case to cure to an elastomeric film. The resulting elastomeric film was then tested for its physical properties after a cure of 24 hours at room temperature and the results are listed in Table II below. Another 6 mil thickness film was also prepared in the same way which film was also cured at room temperature 16 hours and then heated for 1 hour at 95°C in an oven. At the end of that time, the film that had been so heat cured in the oven for 1 hour at 95°C was also tested for its physical properties and the test results are listed in Table II below.

Table II

| Cure | 24 hrs. at R.T. | 16 hrs. at R.T. + 1 hr. at 95°C |
|---|---|---|
| Tensile, psi | 900 | 950 |
| Elongation, % | 850 | 850 |
| Durometer A | 24 | 27 |
| Tear, lbs/in. | 150 | 150 |
| Specific Gravity | 1.13 | 1.13 |

The results in Table II indicate that organopolysiloxane elastomeric compositions prepared in accordance with the present invention have outstanding physical properties both prior to and after heat aging even in thickness as small as 6 mils which make the compositions of the instant case iminently suitable for forming envelopes or casing materials for orthopedic or prosthetic devices, as well as protective coatings for various surfaces.

EXAMPLE 3

There was mixed 80 parts of a polymer of the formula,

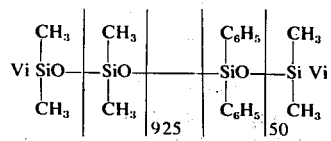

with 20 parts of a low viscosity blend of vinyl-containing polysiloxanes of the formulas,

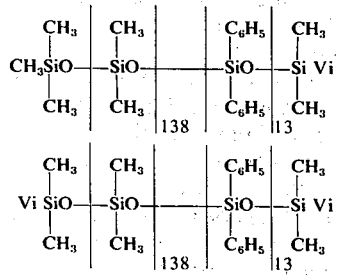

The low viscosity vinyl-containing polymer was a blend of the two compounds shown above. With 100 parts of the above compounds there was mixed into them 40 parts of silazane treated filler which was treated as disclosed in Smith, U.S. Pat. No. 3,635,743. To this mixture there was added 7 parts per million of platinum as a platinum complex such as that disclosed in U.S. Pat. No. 3,220,972, Lamoreaux. The resulting mixture was Component A. To 100 parts of Component A there was mixed 10 parts of Component B which comprised 2 parts of a silicone resin having $H(CH_3)_2SiO_{1/2}$ units and $SiO_2$ units and as identified in Example 1; 2 parts of the same silazane treated filler as was used on Component A; and 6 parts of the high viscosity vinyl-containing polysiloxane used in Component A above.

The two parts Component (A) and (B) were mixed together and placed in a 70 mil ASTM mold and press cured 1 hour at 100°C. The cured elastomer had the following physical properties:

TABLE III

| Properties | 1 hr. at 100°C |
|---|---|
| Tensile Strength (psi) | 1100 |
| Elongation (%) | 950 |
| Durometer-Shore A | 45 |
| Tear, pi | 250 |
| Specific Gravity | 1.17 |

EXAMPLE 4

There was mixed with 87.5 parts of the high viscosity vinyl-containing polysiloxane of Example 1, 12.5 parts of the low viscosity blend of vinyl-containing polysiloxane of Example 1. To this mixture there was added 30 parts of fumed silica and 7 parts per million of a platinum catalyst present as a platinum complex such as that disclosed in U.S. Pat. No. 3,220,972, Lamoreaux. To 100 parts of this composition which shall hereinafter be referred to as Component A, there is mixed into it 10 parts of a composition that was the same as Component B of Example 3. The resulting mixture was press cured for 1 hour at 100°C in a 70 mil ASTM mold. The cured elastomer had the following physical properties shown in Table IV below:

TABLE IV

| Cure | 1 hr. at 100°C |
|---|---|
| Tensile Strength (psi) | 950 |
| Elongation(%) | 1000 |
| Durometer, Shore A | 24 |
| Tear, pi | 175 |
| Specific Gravity | 1.13 |

We claim:

1. A process for producing organopolysiloxane elastomers having high strength with exceptionally good elongation comprising (a) mixing per 100 parts of a mixture which is formed by mixing (i) 20 to 90 parts of a polymer selected from the class consisting of vinyl-containing high viscosity organopolysiloxane and a blend of vinyl-containing high viscosity organopolysiloxane having no more than 25 mole percent of phenyl radicals and having a viscosity of 5,000 to 500,000 centipoise at 25°C of the formula,

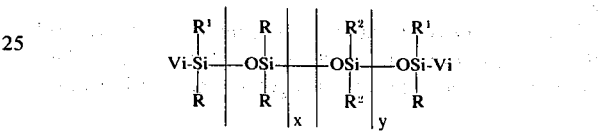

where Vi stands for vinyl, $R^1$ is selected from the class consisting of lower alkenyl, alkyl and aryl radicals, and R is selected from the class consisting of monovalent hydrocarbon radicals and halogenated monovalent hydrocarbon radicals, $R^2$ is selected from the class consisting of alkyl and aryl radicals, $x$ varies from 100 to 10,000, $y$ varies from 0 to 300; (ii) from 5 to 40 parts of a polymer selected from the class consisting of a low viscosity vinyl-containing organopolysiloxane and a blend of low viscosity vinyl-containing organopolysiloxanes having a vinyl content that may vary from 0.01 mole percent to 60 mole percent vinyl and a viscosity that varies from 50 to 50,000 centipoise at 25°C and having no more than 25 mole percent phenyl radicals of the formula,

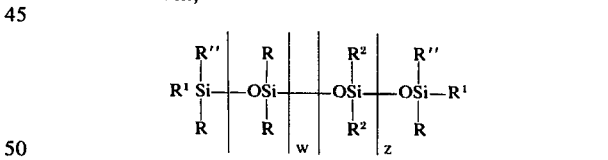

wherein $R^1$, $R^2$ and R are as previously defined, R'' is selected from the class consisting of alkyl, aryl, and alkenyl radicals, $w$ varies from 0 to 500 and $z$ varies from 0 to 200; (iii) from 5 to 70 parts of a filler; (iv) from 0.1 to 100 parts per million of the total composition of a platinum catalyst, and there is mixed as aforesaid into 100 parts of the above mixture, 1 to 100 parts of a hydride silicone compound selected from the class consisting of hydrogen containing silanes and hydrogen containing polysiloxanes and mixtures thereof; and (b) allowing the mixtures to cure at a temperature in the range of 20° to 300°C.

2. The process of claim 1 wherein the mixture is allowed to cure at room temperature for 24 hours.

3. The process of claim 1 wherein the hydrogen containing polysiloxane is a polysiloxane resin having therein $H(R^3)_2SiO_{1/2}$ units and $SiO_2$ units where the ratio of monofunctional units to tetrafunctional units may vary from 0.5:1 to 10:1, the hydroxyl content of the resin is less than 0.5 weight percent and $R^3$ is selected from the class consisting of hydrogen, monovalent hydrocarbon radicals, and halogenated monovalent hydrocarbon radicals.

4. The process of claim 1 wherein hydrogen containing polysiloxanes has the formula,

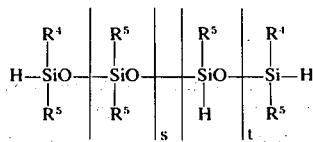

wherein $R^4$ is selected from the class consisting of hydrogen, monovalent hydrocarbon radicals and halogenated monovalent hydrocarbon radicals, $R^5$ is selected from the class consisting of monovalent hydrocarbon radicals and halogenated monovalent hydrocarbon radicals, $s$ varies from 1 to 1000 and $t$ varies from 5 to 200.

5. The process of claim 1 wherein the mixture and silicone compound are first dissolved in solvent, then the two solutions are mixed together and further comprising applying the solutions to an object and allowing the solvent to evaporate so as to have a coating of said high strength organopolysiloxane.

6. The process of claim 5 wherein the solvent is selected from the class consisting of hexane, pentane, octane, cyclohexane, toluene, xylene, benzene, and acetone.

7. The process of claim 1 wherein in the high viscosity vinyl containing organopolysiloxane $R^1$ and R are methyl, $R^2$ is phenyl, $x$ varies from 500 to 2000 and $y$ varies from 0 to 100.

8. The process of claim 1 wherein the low viscosity vinyl containing organopolysiloxane $R^1$ is selected from the class consisting of vinyl and methyl, $R''$ is methyl, R is methyl, $R^1$ is phenyl, $w$ varies from 50 to 300 and $z$ varies from 0 to 100.

9. The process of claim 1 wherein the filler is a treated filler and is selected from the class consisting of titanium dioxide, lithopone, zinc oxide, zirconium silicate, silica aerogel, iron oxide, diatomaceous earth, calcium carbonate, fumed silica, silazane treated silica, precipitated silica, glass fibers, magnesium oxide, chromic oxide, zirconium oxide, aluminum oxide, alpha quartz, calcined clay, asbestos, carbon, graphite, cork, cotton and synthetic fibers.

* * * * *